United States Patent
Predovich

(10) Patent No.: US 10,820,853 B2
(45) Date of Patent: Nov. 3, 2020

(54) SENSOR AND APPARATUS FOR MEASUREMENT OF MUSCLE ACTIVITY IN THE DETECTION AND TREATMENT OF BRUXISM DISORDER

(71) Applicant: Bravrr, LLC, Albuquerque, NM (US)

(72) Inventor: Brock Predovich, Canon City, CO (US)

(73) Assignee: Bravrr, LLC, Albuquerque, NM (US)

( * ) Notice: Subject to any disclaimer, the term of this patent is extended or adjusted under 35 U.S.C. 154(b) by 361 days.

(21) Appl. No.: 15/912,969

(22) Filed: Mar. 6, 2018

(65) Prior Publication Data
US 2018/0353122 A1 Dec. 13, 2018

Related U.S. Application Data

(60) Provisional application No. 62/517,304, filed on Jun. 9, 2017.

(51) Int. Cl.
*A61B 5/00* (2006.01)
*A61B 5/0492* (2006.01)
*A61B 5/22* (2006.01)

(52) U.S. Cl.
CPC .......... *A61B 5/4557* (2013.01); *A61B 5/0492* (2013.01); *A61B 5/228* (2013.01); *A61B 5/6815* (2013.01); *A61B 5/486* (2013.01); *A61B 5/682* (2013.01); *A61B 5/6831* (2013.01); *A61B 5/6838* (2013.01)

(58) Field of Classification Search
CPC .......... A61B 5/11; A61B 5/228; A61B 5/1107; A61B 5/4557; A61B 5/6814; A61F 2005/563
See application file for complete search history.

(56) References Cited

U.S. PATENT DOCUMENTS

| | | |
|---|---|---|
| 4,715,367 A | 12/1987 | Crossley |
| 4,838,283 A | 6/1989 | Lee |
| 4,934,378 A | 6/1990 | Perry |
| 4,976,618 A | 12/1990 | Anderson |

(Continued)

FOREIGN PATENT DOCUMENTS

| | | |
|---|---|---|
| CN | 107518952 A | 12/2017 |
| WO | 1998031277 A1 | 7/1998 |

OTHER PUBLICATIONS

Dinesh, Akshaya, et al, Applications of E-textile Pressure Sensors, Jul. 21, 2017, downloaded from http://soe.rutgers.edu/sites/default/files/imce/gov2017/Applications%20of%20E-textile%20Pressure%20Sensors.pdf on Feb. 1, 2018.

(Continued)

*Primary Examiner* — Daniel L Cerioni
*Assistant Examiner* — Raymond P Dulman
(74) *Attorney, Agent, or Firm* — Richard A. Baker, Jr.

(57) ABSTRACT

An apparatus and method for detecting and reducing bruxism is described. The method includes the placement of a pressure resistive (or piezoelectric) sensor on the skin above the temporalis muscle in order to detect grinding of the teeth based on movement of the temporalis muscle. Alternatively, a pressure resistor could be used in the ear. The pressure resistive sensor could be made of carbon-impregnated polyolefin. Once bruxism is detected, a patient is notified and uses bio-feedback to curtain the grinding of the teeth.

19 Claims, 17 Drawing Sheets

(56) References Cited

U.S. PATENT DOCUMENTS

| | | | |
|---|---|---|---|
| 5,078,153 | A | 1/1992 | Nordlander et al. |
| 5,553,626 | A | 9/1996 | Burger et al. |
| 6,117,092 | A | 9/2000 | Weinstein et al. |
| 6,544,199 | B1 | 4/2003 | Morris |
| 9,816,882 | B2 * | 11/2017 | Zhang ................. G01L 1/18 |
| 2004/0059212 | A1 * | 3/2004 | Abreu ................. A61B 5/01 600/373 |
| 2005/0113710 | A1 | 5/2005 | Stahmann et al. |
| 2006/0184059 | A1 | 8/2006 | Jadidi |
| 2007/0112277 | A1 | 5/2007 | Fischer et al. |
| 2011/0125063 | A1 | 5/2011 | Shalon et al. |
| 2011/0288445 | A1 | 11/2011 | Lillydahl et al. |
| 2013/0041235 | A1 * | 2/2013 | Rogers ............... A61B 5/1107 600/306 |
| 2014/0107452 | A1 * | 4/2014 | Wu ..................... A61B 5/04 600/372 |
| 2015/0038881 | A1 | 2/2015 | Gokhale et al. |
| 2017/0128000 | A1 * | 5/2017 | Martin ................ A61B 5/6833 |

OTHER PUBLICATIONS

Wu, Qizong, et al, Smart Glove Design Using Smart Materials Sensors and Actuators, downloaded from https://seelio.com/w/28c6/smart-glove-design-and-implementation-using-smart-materials on Feb. 1, 2018.

Dordevic, Srdan, MC Sensor—A Novel Method for Measurement of Muscle Tension, Sensors (Basel), v.11(10), 2011.

Lukowicz, Paul, et al, Detecting and Interpreting Muscle Activity with Wearable Force Sensors, International Conference on Pervasive Computing, 2006, pp. 101-116.

Han, Hyonyoung, et al, Novel muscle activation sensors for estimating of upper limb motion intention, Engineering in Medicine and Biology Society, 2009. EMBC 2009. Annual International Conference of the IEEE.

Gu, WeiPing, et al, Efficacy of biofeedback therapy via a mini wireless device on sleep bruxism contrasted with occlusal splint: a pilot study, Journal of Biomedical Research, Apr. 2015; 29(2): 160-168.

Criado, Laura, et al, Electromyographic biofeedback training for reducing muscle pain and tension on masseter and temporal muscles: A pilot study, Journal of Clinical and Experimental Dentistry, Dec. 2016; 8(5): e571-e576.

Sato, M, et al, Electromyogram biofeedback training for daytime clenching and its effect on sleep bruxism, Journal of Oral Rehabilitation, Feb. 2015;42(2):83-9.

Shetty, Shilpa, Bruxism: A Literature Review, J Indian Prosthodont Soc. Sep. 2010; 10(3): 141-148.

Trindade, M, et al, Interdisciplinary treatment of bruxism with an occlusal splint and cognitive behavioral therapy, Gen Dent. Sep.-Oct. 2015;63(5):e1-4.

* cited by examiner

SENSOR AND APPARATUS FOR MEASUREMENT OF MUSCLE ACTIVITY IN THE DETECTION AND TREATMENT OF BRUXISM DISORDER

CROSS REFERENCE TO RELATED APPLICATIONS

This application is a non-provisional Application, for which priority is claimed under 35 U.S.C. § 119, of U.S. Provisional Patent Application No. 62/517,304, filed Jun. 9, 2017, and entitled "Sensor & Apparatus for Measurement of Muscle Activity in the Detection & Treatment of Bruxism (Teeth Clenching/Grinding) Disorder," the entire content of the above provisional patent application is incorporated herein by reference in its entirety.

BACKGROUND

Technical Field

The devices described herein are directed to the detection of Bruxism Disorder, and more specifically to sensors and apparatuses for the detection and treatment of teeth clenching and grinding.

Description of the Related Art

Bruxism is an oral parafunction characterized by clenching and grinding of teeth during wakefulness or sleep. Bruxism is a common behavior; reports of prevalence range from 8-31% in the general population. Several symptoms are commonly associated with bruxism, including hypersensitive teeth, aching jaw muscles, headaches, tooth wear, and damage to dental restorations crowns and to teeth. But symptoms may be minimal, without patient awareness of the condition.

There are two main types of bruxism: one occurs during sleep (sleep bruxism) and one during wakefulness (awake bruxism), Dental damage may be similar in both types, but the symptoms of sleep bruxism tend to be worse on waking and improve during the course of the day, and the symptoms of awake bruxism may not be present at all on waking, and then worsen over the day. The causes of bruxism are not completely understood, but probably involve multiple factors. Awake bruxism is thought to have different causes from sleep bruxism, and is more common in females, whereas males and females are affected in equal proportions by sleep bruxism. Several treatments are in use, although there is little evidence of robust efficacy for any particular treatment.

A number of causes of Bruxism have been identified. Mental disorders, anxiety, stress and adverse psychosocial factors are significantly related to tooth grinding during sleep and it has been found that nearly 70% of bruxism occurs as a result of stress or anxiety. Bruxism can be a side effect of certain medications, including some antidepressants and antipsychotics, and amphetamines. Neurological conditions such as Huntington's disease or Parkinson's disease can also cause it. Other factors that may be related include fatigue, alcohol consumption, smoking, sleep apnea, and snoring. Research has shown that it's a sleep disturbance that originates in the central nervous system, and it's not triggered or controlled by peripheral factors in the mouth, like an occlusion, i.e. a blockage of some sort, or tooth contacts. Bruxism is not caused by infectious disease as people used to think, nor is it a tic or reaction triggered by improperly fixed dental prostheses.

Treatment modalities for bruxism involve reversible occlusal correction, behavioral changes and pharmacological approaches. The most common method of reversible occlusal adjusting for many bruxers is the use of occlusal appliance. However, the inherent effect of an occlusal splint has been found to be the protection of tooth wear rather than the alleviation of bruxism behavior itself. One of the behavioral approaches is the biofeedback method for bruxism; the efficacy has been reported by many researchers. The majority of these devices rely on electromyography (EMG) of the masticatory muscles.

However, there are some disadvantages of EMG biofeedback devices, i.e., the EMG signals can be affected by electrode position, posture and skin resistance. It is also difficult for bruxers to tolerate the device well while asleep with the electrodes attached on masseter and/or temporalis muscles. So far, there is no approach that is effective fir bruxism management.

Current solutions on the market to detect muscle activity/muscle activation rely on expensive EMG (Electromyography) sensors technology. Additionally, detecting muscle activity during bruxism (unconscious teeth grinding) remains difficult because it is hard to find and maintain a strong sensor signal outside of the lab environment. Sensors don't stick well, the user sweats, or the sensor shifts position and no longer remains in the place to detect muscle activity.

The present invention, through various methods, is directed, through a wearable device, to detect variations in muscle activity using piezoelectric discs, pressure-sensitive discs, force-sensitive discs, piezoelectric film and force resistive sensors. The present invention is designed to utilize these inexpensive sensor to detect muscle activity during the occurrence of bruxism behavior and also describe the means of initiating a biofeedback response to change, reduce, or eliminate bruxism disorder in the wearer.

The present invention, eliminates the issues articulated above as well as other issues with the currently known products.

SUMMARY OF THE INVENTION

A method of detecting bruxism made up of the steps of arranging a pressure resistive sensor next to the skin above the temporalis muscle. The pressure resistive sensor is comprised of a carbon-impregnated polyolefin material. The polyolefin material has a conductive surface attached to the top side and the bottom side. Both conductive surfaces have wires connected to them. When the temporalis muscle moves, the polyolefin sensor senses the movement. The movement information is transmitted through the wires to a special purpose microprocessor. Finally, the microprocessor analyzes the movement information to determine if bruxism is occurring. In some embodiments, multiple layers of the polyolefin material is stacked on top of each other, and these layers could be adhered with an adhesive. There could be at least five layers of polyolefin material. The polyolefin sensor could mounted on a headband, and once bruxism is detected, the special purpose microprocessor could provide biofeedback, perhaps through sound coming from a speaker.

A muscle contraction sensor comprising a carbon-impregnated polyolefin material with a conductive surface on the top and bottom of the material, and wire connected to each conductive surface, wherein the bottom side of the polyolefin material is placed proximate to skin above the muscle. The polyolefin material could be multiple layers of the polyolefin material stacked on top of each other, and these layers could be adhered with an adhesive. There could be at least five layers of polyolefin material. The muscle could be the temporalis muscle. The polyolefin sensor could mounted on a headband, or the sensor could be attached to the skin with an adhesive. The wires could be connected to a special purpose microprocessor, and the microprocessor could determine if bruxism symptoms are seen in the muscle. The special purpose microprocessor could provide biofeedback through a biofeedback device.

A pressure sensor comprising polyolefin material wherein the polyolefin material comprises multiple carbon-impregnated polyolefin surfaces adhered together. A first conductive surface attached to one side of the polyolefin material and a second conductive surface attached to a second side of the polyolefin material. A first wire connected to the first conductive surface and a second wire connected to the second conductive surface. The multiple carbon-impregnated polyolefin surfaces could be adhered with an adhesive. The polyolefin material could comprise at least five carbon-impregnated polyolefin surfaces.

DETAILED DESCRIPTION OF THE INVENTION

The invention of a bruxism detection and biofeedback device can be constructed using three variations of the sensor apparatus. We will discuss these sensor variations and optimal placement of these sensors in the text below. The "Sticky Piezo Disc Muscle Sensor", the "Sticky Piezo Film Muscle Sensor" and the "Force Sensitive Resistor In-Ear Sensor" described below all work to detect physiological changes wearer (user, patient, individual being sensed) exhibits during clenching or grinding activity.

The apparatus and methods described below can also be used for Apnea and Snoring. By placing a sensor on the bottom part of the ear next to the jaw bone, the sensor is able to detect when the jaw is open or closed, therefore, detecting the movements involved in apnea and snoring activities.

The Sticky Piezo Disc Muscle Sensor (FIGS. 1, 2, 16 and 17) is comprised of a piezoelectric disc 102, 103, mounted on an elongated, thin, rigid, but flexible plastic material 101. The rough length of the plastic material 101 should be roughly 2 to 3 times the piezoelectric disc's 102, 103 diameter. The width should not extend more than a few centimeters past the piezoelectric disc's 102, 103 diameter. The plastic 101 can be a rounded corner rectangle or more optimally an elongated oval shape is preferred for comfort. The wired piezoelectric disc 102, 103 is then mounted in the center of the plastic 101. The mounted piezoelectric disc 102, 103 and plastic (the "Piezo Disc Muscle Sensor") 101, once placed over the desired muscle, work to sense the muscle's contraction by detection pneumatic changes in the shape and tension of the surface skin.

Figure 1:
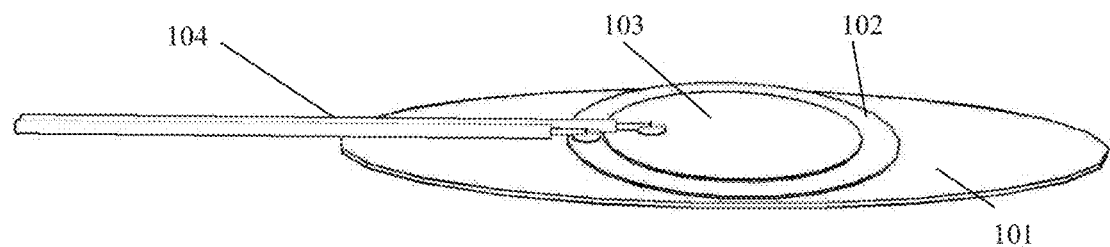
FIG. 1 shows the Sticky Piezo Disc Muscle Sensor mounted to Flexible Plastic, perspective view.

Specifically looking to FIG. 1, there is a perspective view of the piezoelectric sensor. The flexible plastic base 101 is made of a thin material that connects to the user's skin. In some embodiments, the plastic base 101 has an adhesive material (such as a silicone reusable adhesive) on the back side to adhering the plastic to the user's skin. In another embodiment, an adhesive could be sprayed on the user's skin to hold the plastic 101. In another embodiment, the plastic 101 could be missing entirely, with the piezoelectric disc 102 adhered directly to the user's skin. In still another embodiment, a moldable ear clamp mechanism is used to keep the sensor in place. Basically, a plastic housing for the electronics and sensor on top of the ear and then an 14 to 18 gauge wire on the bottom that can be molded to the size of the ear 'clamping' the device in place.

Figure 22:
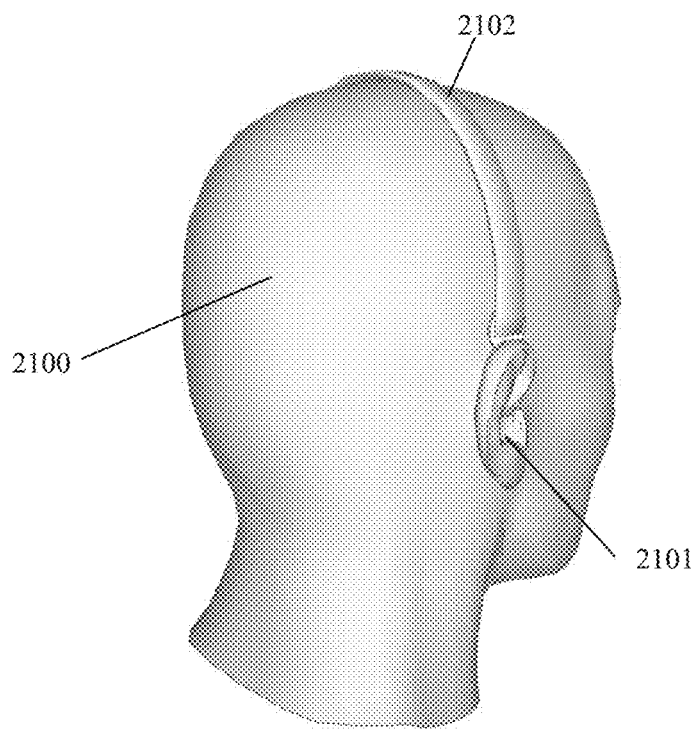
FIG. 22 shows a Method of Placement of the Piezo Disc/Force Sensitive Resistor Hairband Dual Single Sensor & Dual Sensor Array from a rear perspective view.

The piezoelectric disc has a top 103 and a bottom 102 surface, each connected with an electrical wire 104 that provides the piezoelectric strain value to a processor 2302, as seen in FIG. 22.

Commercial piezoelectric sensors create a parallel plane with air as a dielectric material, in which after operating for a short amount of time the exhibits parasitic capacitance which prevents signal change, thus renders the transducer circuit unusable. The solution to the capacitance problem is to add a shunt electronic switch (i.e. MOSFET) and periodically bypassing the piezoelectric disc transducer leads to rapidly discharge internally accumulated parasitic capacitive charge. Nonetheless, this approach is not without drawbacks, namely increasing the circuit complexity and increasing ADC timing sensitivity. The analog to digital converter (ADC) in FIG. 22 is located within the special purpose microprocessor system on a chip 2302. The ADC converts the voltage received from the piezoelectric sensor into a numeric value for processing by the special purpose microprocessor.

In one embodiment, the piezoelectric disc (or the piezoelectric sensor) is instead made of a pressure resistive material. In some embodiments, the pressure resistive material is woven conductive fabric such as Shieldex Bremen Kassel, Nora, or Zell product lines or the fabrics from LessEMF. In another embodiment, the pressure resistive material could be a carbon impregnated foam such as Antistat's Conductive Form, or Plastazote Foam. These foams could be made of polyethylene or polyurethane The pressure resistive material could also be a volume-conductive, carbon-impregnated polyolefin such as Velostat from 3M or Linqstat from Caplinq. Velostat (and other carbon-impregnated polyolefin products) is a piezoresistive or pressure resistive or force resistive material, meaning the electrical resistance decreases when pressured. When sandwiched between two conductive layers, it has a broad resistive range for making pressure and bend sensors.

Velostat (and other carbon-impregnated polyolefin products) is purely resistive (i.e. negligible parasitic capacitance), thus changes in pressure can be directly picked up as voltage drop on a second resistor in a series voltage divider circuit. Velostat can be modeled as a variable resistor where its resistance are inversely proportional with the pressure applied on it. Velostat is an anisotropic material which has different resistance between its surfaces measured top to bottom side) and its internal lattice structure (i.e. measured on two points on the same side).

Two Velostat strips stacked against each other yields too large a variance with different strip sizes and modest pressure sensitivity with effective resistance "swing" of several hundred kilo-ohms. This lack of sensitivity is caused by the internal lattice resistance, which is only sensitive to direct pressure on specific points, contributes to most of the effective resistance between measurement electrodes.

Figure 26:
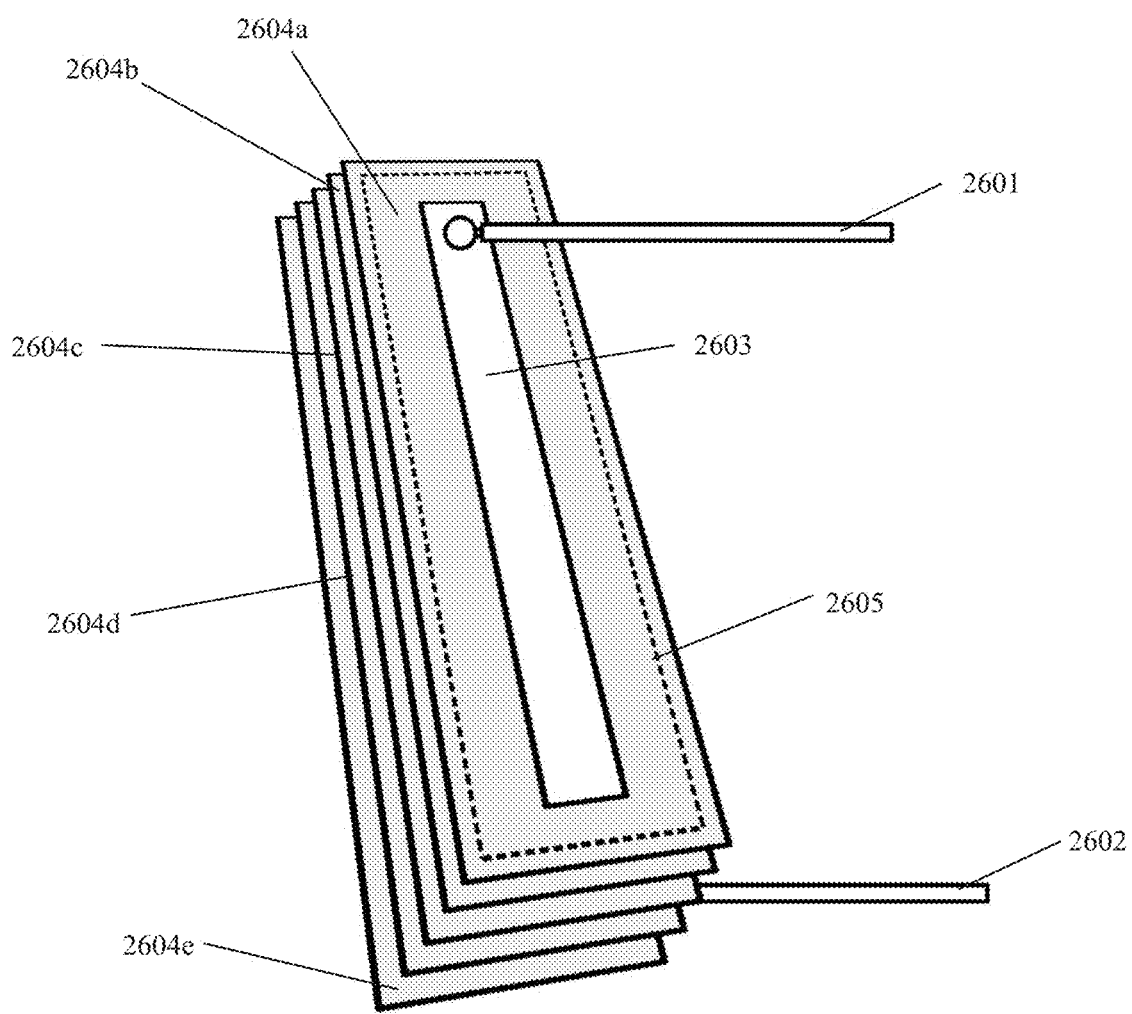
FIG. 26 is a view of a stack of carbon-impregnated polyolefin arranged as a pressure sensor.

One embodiment, seen in FIG. 26, uses Velostat strips in multiple (five or more) layer stacks in-between top and bottom layer, also using elongated electrodes using conductive tapes. This structure proves to have a very large swing (tens of mega-ohms) and more uniform swing along the length of the transducer strip. This uniformity picks up muscle contraction more reliably regardless of variation in muscle structure of every individual user and sensor placement.

Figure 27:
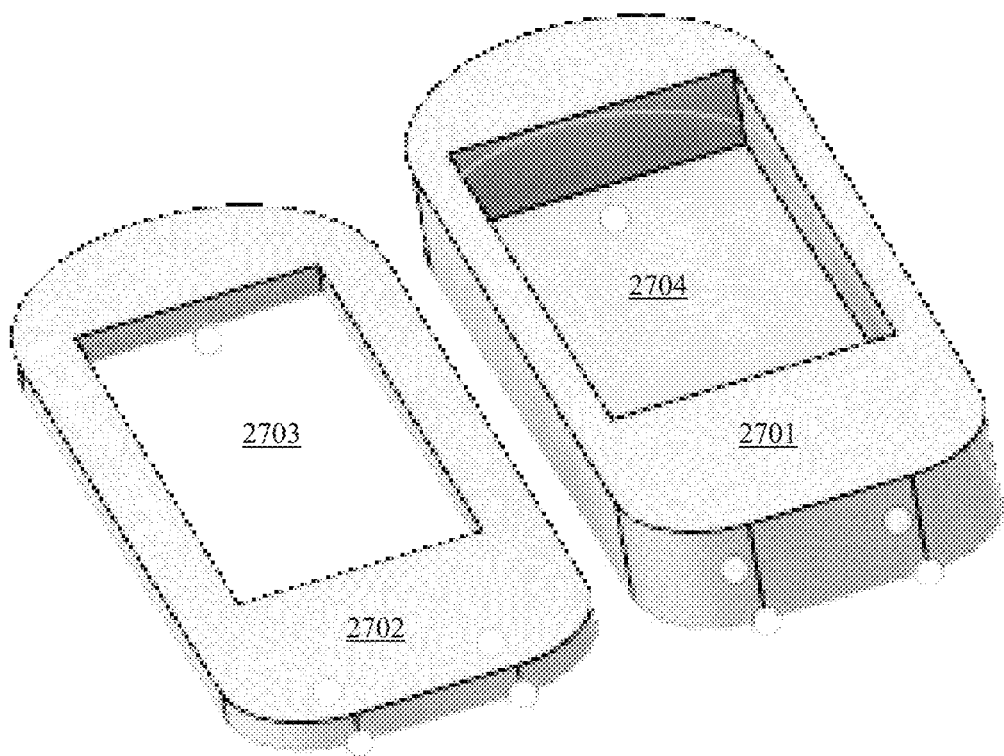
FIG. 27 is a view of a housing for a stack of carbon-impregnated polyolefin surfaces.

In one embodiment, seen in FIG. 27, a loose stack of carbon-impregnated polyolefin layers is used, where the layers are enclosed in a plastic base 2701. A pocket 2704 holds the stack of carbon-impregnated polyolefin material. The first layer on the bottom will have the electrode attached with electrode side facing the bottom plastic base 2704. Then 16 to 20 layers of carbon-impregnated polyolefin material will be stacked on top of each other. The top layer will have another electrode facing out. The plastic cap 2702 goes on top of the base 2701 to secure all the layers. The cap 2702 has a window 2703 to expose the sensor layers to pressure. In one embodiment, there is one more piece (not shown), a piece of plastic the fits inside the window and plunges down with pressure.

In still another embodiment, a loose stack is assembled by having the top and bottom electrode layers, multiple layers in between, then enclosing all layers with a piece of tape.

Looking to FIG. 26, there are two wires 2601 and 2602 connecting to a thin strip of copper tape 2603 on the top and bottom of the stack of carbon-impregnated polyolefin material 2604a-e. In the drawing, five layers of carbon-impregnated polyolefin material 2604a-e are shown. The stack of carbon-impregnated polyolefin material 2604a-e with the copper tape 2603 on the top and bottom (not show in the figure) make up the sensor. The layers of carbon-impregnated polyolefin material 2604a-e are adhered to each other with a grid of double-side adhesive tape or a grid of glue. In one embodiment, the glue or adhesive 2605 is applied between the layers in a line that is slightly inside of the edge of the layers of the polyolefin 2604a-e material, as shown by the dashed line on FIG. 26.

Figure 2:
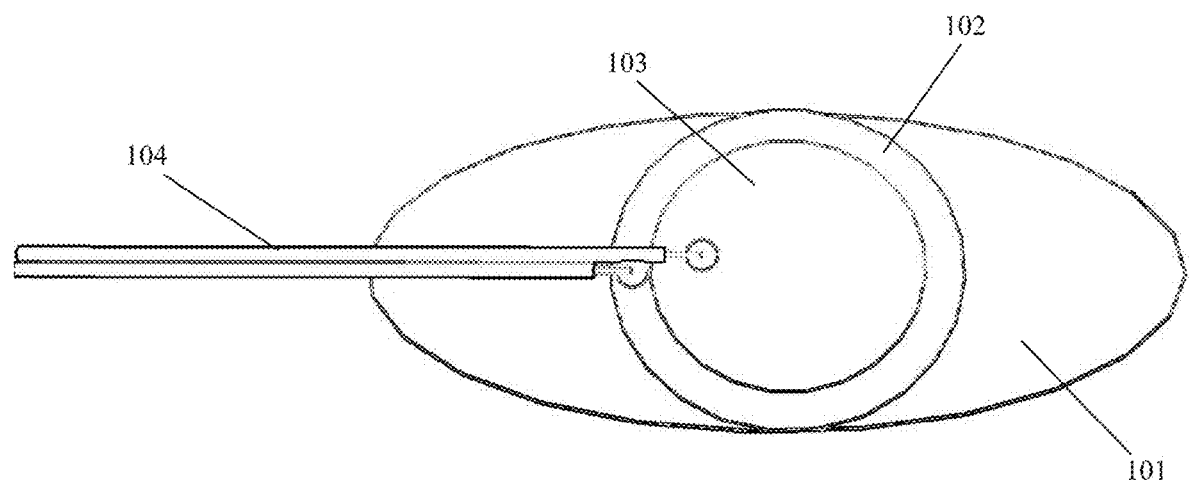
FIG. 2 shows the Sticky Piezo Disc Muscle Sensor mounted to Flexible Plastic, top view.

FIG. 2 is a top view of the piezoelectric sensor. The wires 104 connect to the piezoelectric material at the top 103 and bottom 102. The piezoelectric sensor is connected at the bottom 102 to a thin plastic material 101. For instance, the piezoelectric sensor 102, 103 could be a CUI Inc, 102-1128-ND Piezo sensor or a Rohm Semiconductor Pressure Sensor IC BM1383AGLV.

By placing the piezo disc muscle sensor over wearer's jaw muscles (masseter) or temporalis muscles, one can detect the contraction of these muscles. When the muscle is contracted, the elongated semi-rigid plastic 101 will flex and create a surface pressure on the piezoelectric disc 102 mounted on the plastic's surface 101. This change in surface pressure on the piezoelectric disc 102, 103 creates an electric signal which can be read by any analog input within a controlling micro electronic device 2302. Placement of the piezo disc muscle sensor over the temporalis muscle, just above the ear is the most desired placement in detecting bruxism. The temporalis muscle just above the ear only contracts when the back teeth are clenched or grinding. Therefore the placement of sensor on the temporalis muscle just above the ear negates any interference the sensor would receive due to normal facial movements like talking or facial expression such as raising one's eyebrows.

The Sticky Piezo Film Muscle Sensor (FIGS. 3 and 4) is constructed in a similar fashion as the Piezo Disc Muscle Sensor being mounted to a piece of semi-rigid, flexible plastic 301 in an elongated shape. Piezoelectric film 302,303 is mounted to the plastic 301 in a parallel direction to the elongation of the elongated oval shaped plastic 301 or if plastic is in a rounded corner rectangular shape the piezoelectric film 302,303 should also be mounted in a parallel direction to the length of the rounded corner plastic material 301. This sensor works much like the Piezo Disc Muscle Sensor in that it also detects changes on the surface of the skin over the muscle being sensed. The piezo film 302,303 is bent/flexed while the surface skin bends and flexes during muscle contraction, thereby creating a variation in the electric signal coming from the sensor. As before the sensor can be placed over the wearer's jaw muscles (masseter) or temporalis muscles, but the desired location of placement should be on the temporalis muscle just above the ear to avoid any interference with normal facial activity not related to bruxism's clenching and grinding.

Figure 3:
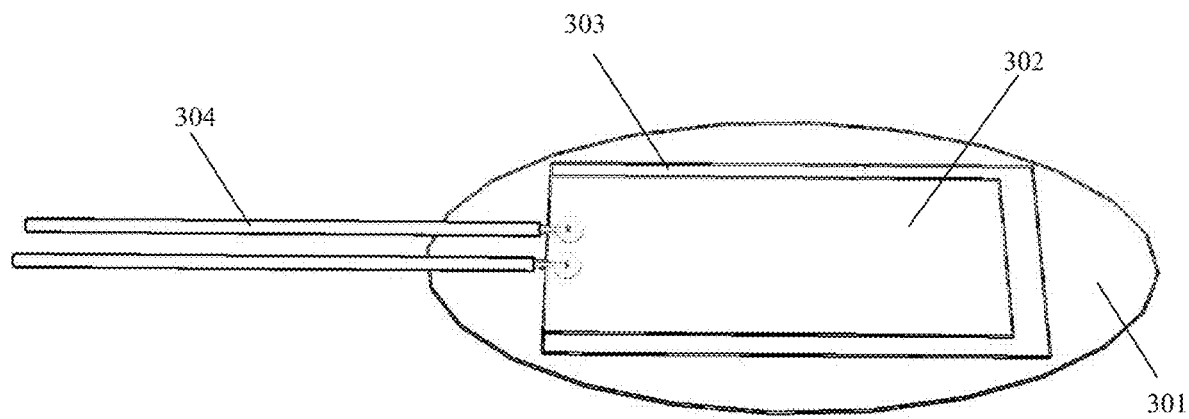
FIG. 3 shows the Sticky Piezo Film Muscle Sensor mounted to Flexible Plastic, top view.
Figure 4:
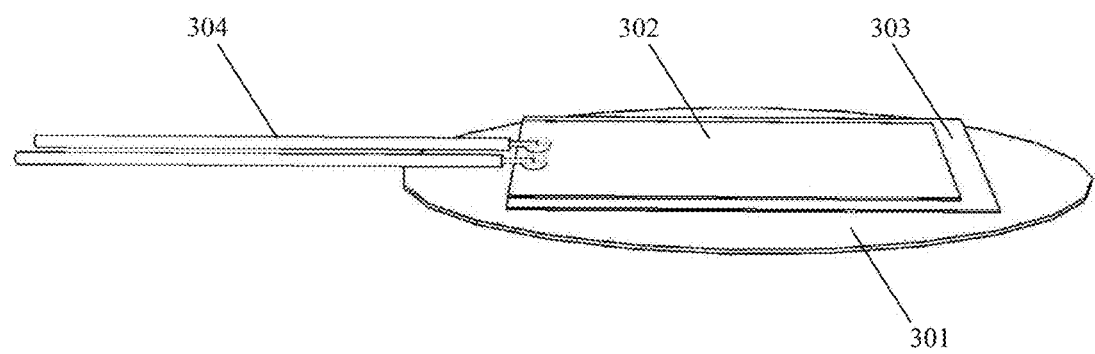
FIG. 4 shows the Sticky Piezo Film Muscle Sensor mounted to Flexible Plastic, perspective view.

FIG. 3 is a top view of the Sticky Piezo Film Muscle Sensor and FIG. 4 is a perspective view. The piezoelectric sensor wires 304 are connected to the piezoelectric film 302,303. The piezoelectric film detects the strain between the top 302 and bottom 303 portions of the piezoelectric film. The bottom of the piezoelectric film is connected to a thin plastic disk 301. The thin plastic 301 could contain an adhesive back for adhering to the patient's skin. Or a user could apply adhesive to either the plastic 301 or directly to the patient's skin.

The piezoelectric film 302,303 could be cut from a TE Connectivity Piezo Film Sheet (part number 1-1004346-0 or 1-1004347-0 with wires 304 soldered to the two metalized sides of the piezo material. A piezoelectiic transducer has very high DC output impedance and can be modeled as a proportional voltage source and filter network. The voltage V at the source is directly proportional to the applied force, pressure, or strain. The output signal is then related to this mechanical force as if it had passed through the equivalent circuit.

The next modality of sensing bruxism events is using a force resistive sensor inside the ear to detect pneumatic pressure/force placed on the sensor while the jaw is clenched or grinds. This Force Sensitive Resistor In-Ear Sensor (FIGS. 5, 6, 7) is constructed by mounting a force resistive sensor 502 on the surface of a foam, rubber or flexible plastic material 501 designed fit snugly within the wearer's ear canal. It should be mentioned, in the case of using foam material, the force sensitive resistor 502 can be mounted on the inside encased inside of the foam 501. The sensor works by detecting the variation of force on the sensor within the ear as the wearer clenches or grinds. When the wearer clenches or grinds there is a subtle change within the structure of the ear canal, a protrusion, because of the temporalis muscle contracting. This creates a pressure on the inserted device. The Force Sensitive Resistor In-Ear Sensor being placed within the ear senses this change in the ear's structure and creates and variation in analog signal.

Figure 5:
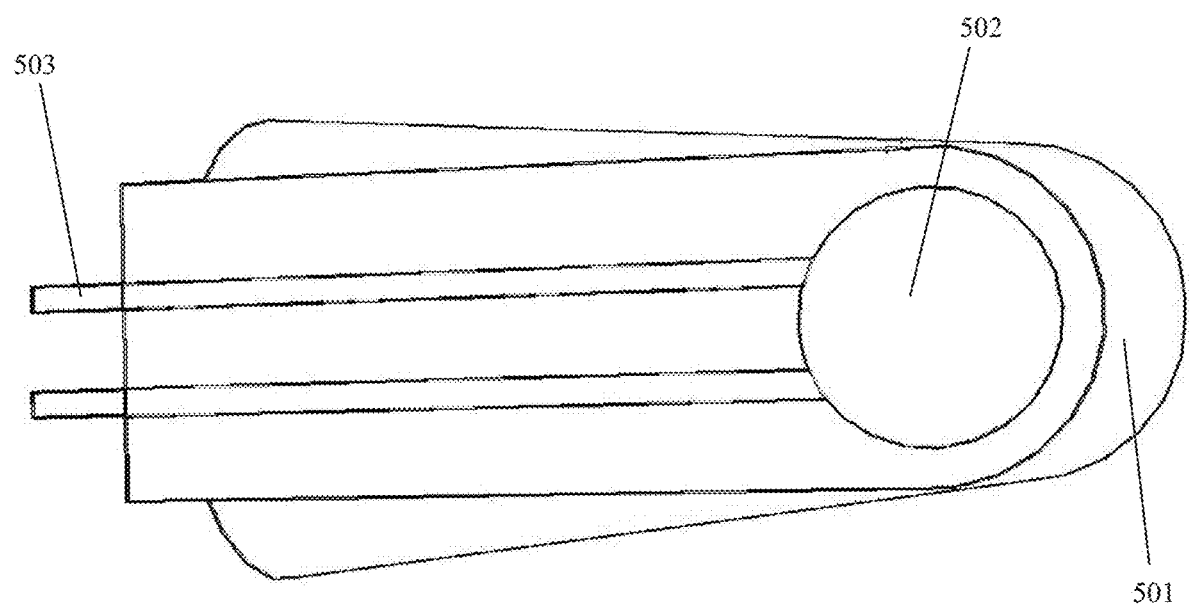
FIG. 5 shows a cross section of the Force Sensitive Resistor In-Ear Sensor-Sensor mounted on surface of foam ear plug, or flexible rubber/silicone ear plug.

Looking to FIG. 5, a cross sectional view of the Force Sensitive Resistor In-Ear Sensor. The sensor 502 is a force sensing resistor, for example an Interlink Electronics FSR 400 Short. The sensor 502 has two leads 503. On one lead, a voltage, say +5 VDC is applied, and the voltage drops across the resistance of the sensor, based on the force applied. For simple force-to-voltage conversion, the FSR device is tied to a measuring resistor in a voltage divider (see figure below) and the output is described by the following equation.

$$Vout = Rm \times V/(Rm+Rf)$$

Where the output voltage Vout is the result of the resistance Rm of a resistor between the force sensitive resistor and ground, multiplied by the supply voltage, divided by the sum of Rm and the resistance of the force sensitive resistor with force applied. See FIG. 23 for the circuit.

The force resistive sensor 502 is placed in a foam ear plug 501. The foam ear plug 501 could be made of foam, flexible rubber, a liquid (or gel) sack, flexible plastic, or any other material that will transfer force from the surface onto the force resistive sensor 502.

Figure 6:
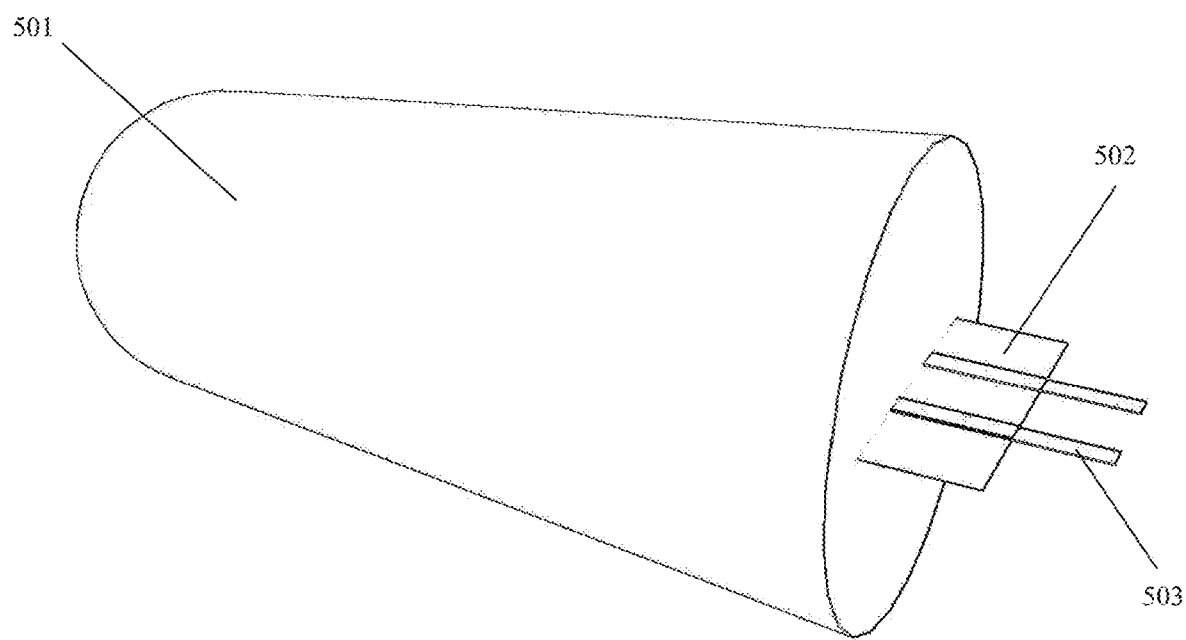
FIG. 6 shows a perspective view of the Force Sensitive Resistor In-Ear Sensor-Sensor enclosed in foam ear plug.

FIG. 6 is a perspective view for the in-ear sensor. In this view, the leads 503 and the foam ear plug 501 are visible. The force resistive sensor 502 is hidden inside of the foam 501.

Figure 7:
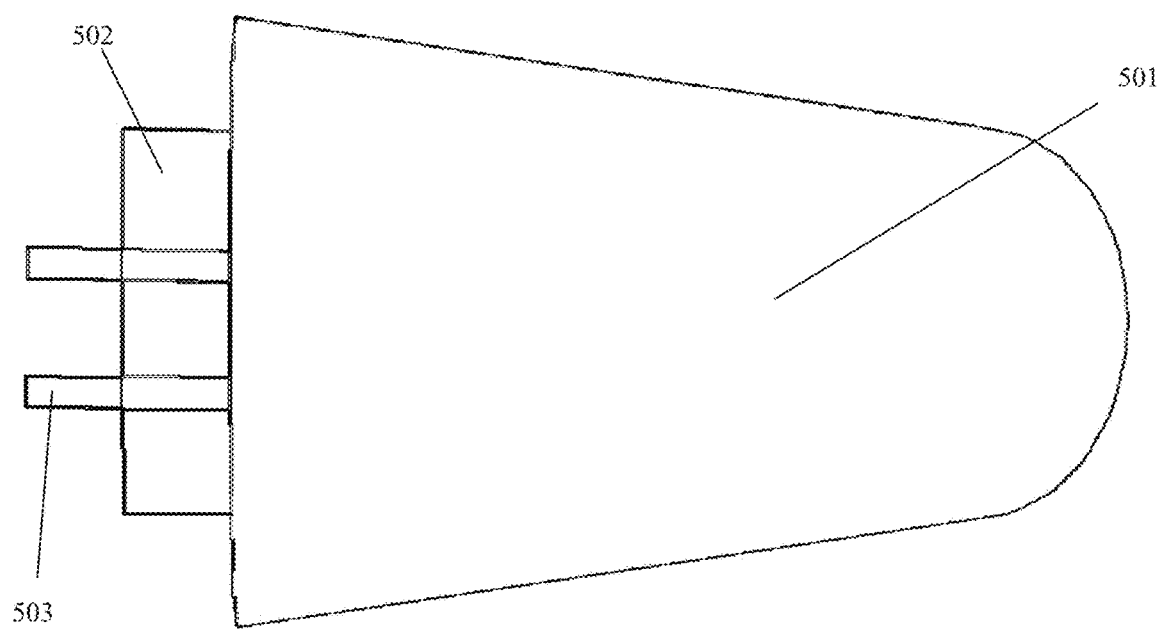
FIG. 7 shows a top view of the Force Sensitive Resistor In-Ear Sensor-Sensor enclosed in foam ear plug.

FIG. 7 is a top view of the in-ear sensor with the leads 503 and the foam 501 showing.

The Piezo Disc Muscle Sensor Encased in Silicone Gel Adhesive (FIGS. 8, 9, 18, 19 and 20) is the next variation of detecting muscle activity. A piezo disc 802,803 can be encased in adhesive silicone 800 and placed over the muscle needing to be sensed or it can be mounted to a thin piece of plastic 801 and then encased in adhesive silicone 800 to give the sensor better signal strength. The piezo muscle sensor 802,803, the microcontroller 805 and the battery 806 can all be encased within the silicone adhesive 800 and made into a shape that fits around the ear so that the user has extreme comfort and the device is non-invasive/non-visible to most people as it will be placed behind the ear.

Figure 8:
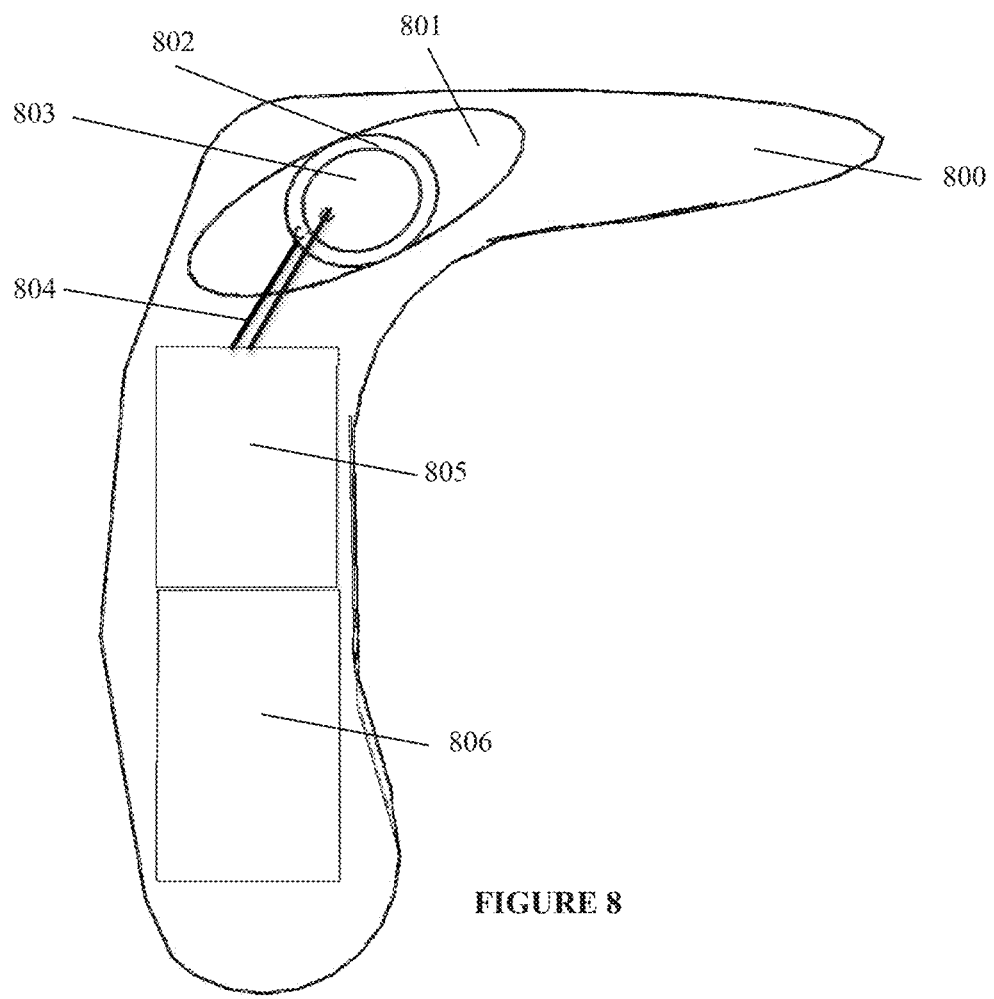
FIG. 8 shows a top view of the Piezo Disc Muscle Sensor Encased in Silicone Gel Adhesive w/Micro Controller & Battery.
Figure 9:
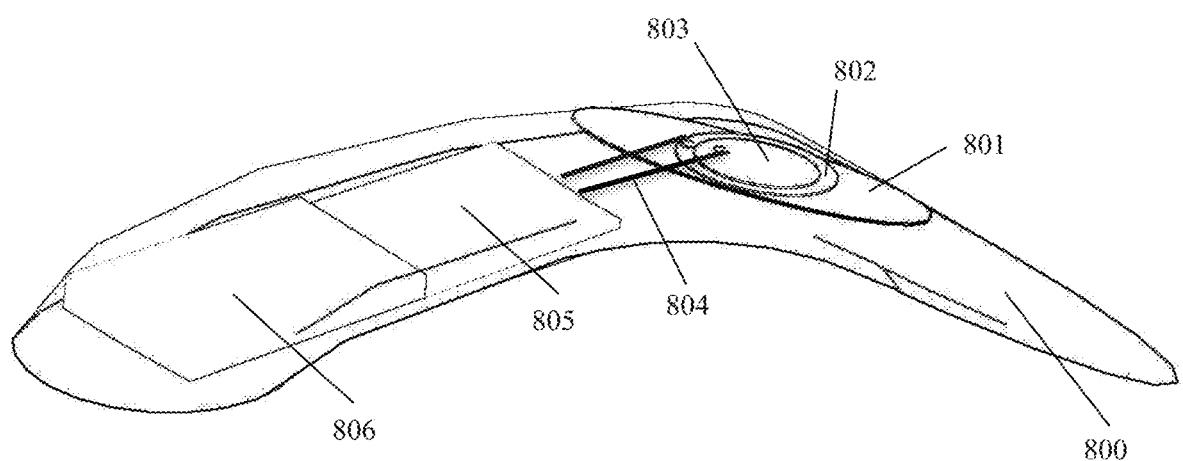
FIG. 9 shows a perspective view of the Piezo Disc Muscle Sensor Encased in Silicone Gel Adhesive w/Micro Controller & Battery.

Looking at the top view in FIG. 8 and the perspective view in FIG. 9, the elements are placed within a silicone gel adhesive 800, Inside of the silicone gel 800 is the piezo sensor 802, 803 that is mounted on a thin piece of plastic 801 in one embodiment. In other embodiments, the piezo sensor 802, 803 is mounted on the wall of the silicone gel sack 800, The piezo sensor 802,803 has two wire leads 804 that electrically and mechanically connect the piezo sensor 802, 803 to the microprocessor assembly 805. The microprocessor assembly 805 is electrically and mechanically connected to the battery 806 by a set of wires (not shown). The wires provide power from the battery 806 to the microprocessor assembly 805. In some embodiments, the battery 805 is removable and replaceable. In other embodiments, the battery is permanent, and the entire sensor assembly is discarded when the battery is discharged. In still another embodiment, the battery 806 is rechargeable through a recharging circuit in the microprocessor circuitry 805. In still another embodiment, the battery 806 is a battery-less power management unit for energy harvesting systems using a technology to harvest vibrations or radio waves, perhaps through a piezoelectric converters.

In another embodiment, the silicone gel sack 800 could be replaced with moldable plastic or similar material.

Figure 23:
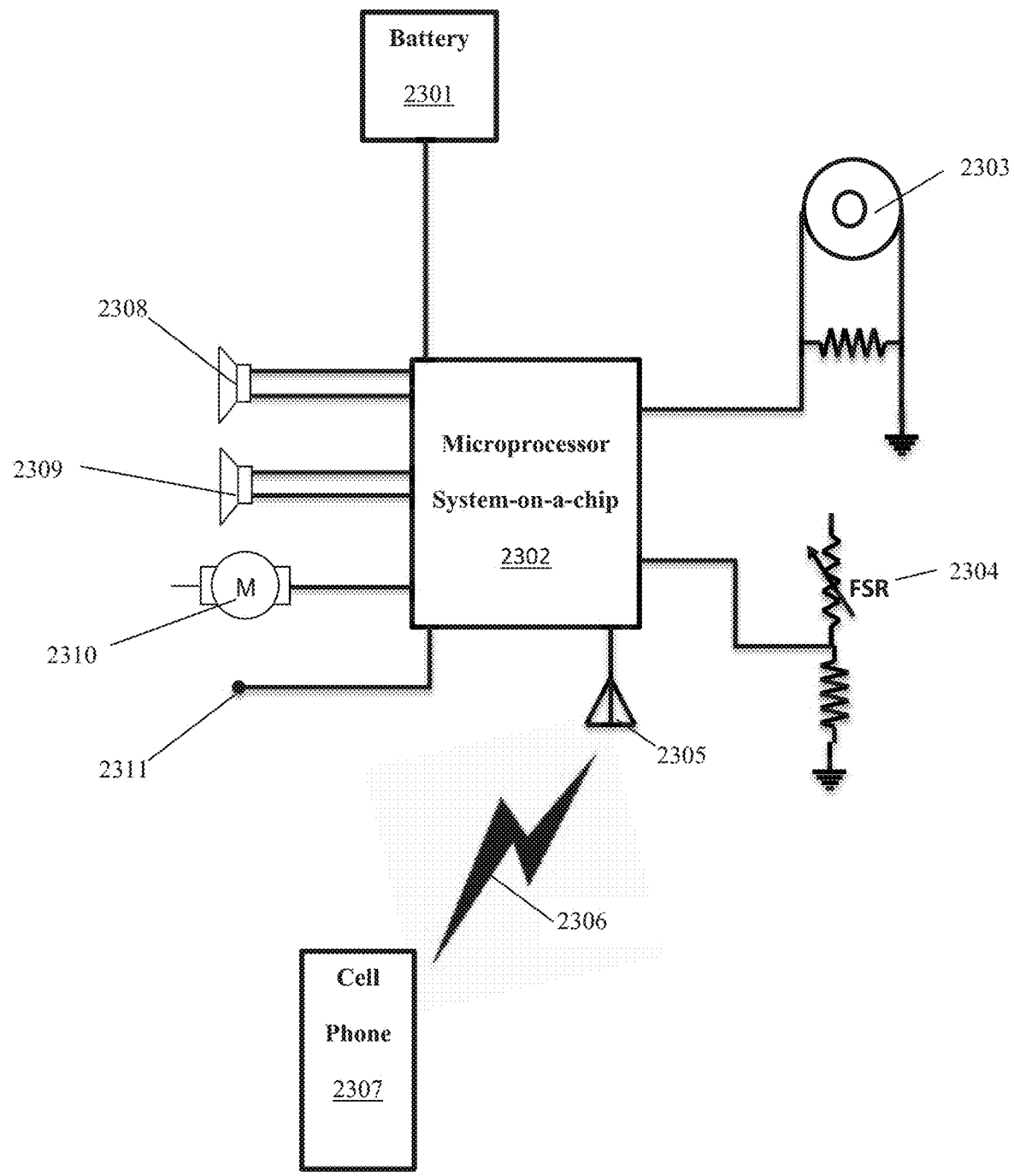
FIG. 23 shows an electrical block diagram for the microprocessor assembly.

The microprocessor assembly 805 is described in further detail in FIG. 23. The microprocessor assembly 805 includes a CPU, interface circuitry for the sensors, an antenna, and circuitry for interfacing to the battery 806. The CPU is likely a special purpose system on a chip design that includes memory, processors, interface circuitry, integrated communications, and built-in software modules.

Another embodiment detects muscle activity: the "Piezo Disc/Force Sensitive Resistor Hairband Dual Single Sensor & Dual Sensor Array" uses a modified hair band 1001 device with two mounts 1002a, 1002b on either side of the band used for mount piezoelectric discs 1203 or force sensitive resistors to measure muscle activity (FIGS. 10, 11, 12, 13, 14, 15, 21 and 22). A thin foam material 1205 or fabric can be mounted on top of the piezo disc 1203 so that the sensor is comfortable as it is press upon the skin with the tension in the band 1001. These dual sensors 1203 will be connected to a microcontroller 1206 and battery 1207 to complete the device. The band's mount can also be elongated to allow for multiple sensors 1402, for example multiple piezo discs 1403a, 1403b, 1403c or multiple force resistive sensors can be mounted and connected in an array to detect muscle activity.

Figure 10:
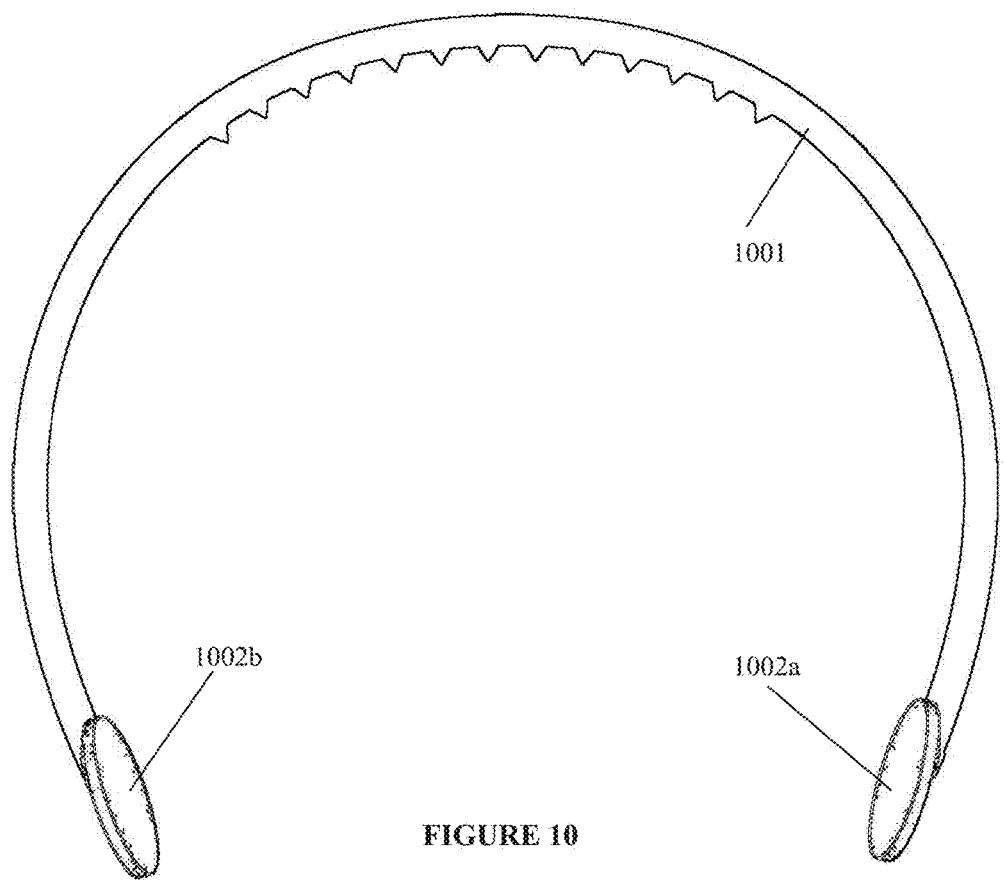
FIG. 10 shows a front view of the Modified Hairband for Dual Sensor & Sensor Array.
Figure 11:
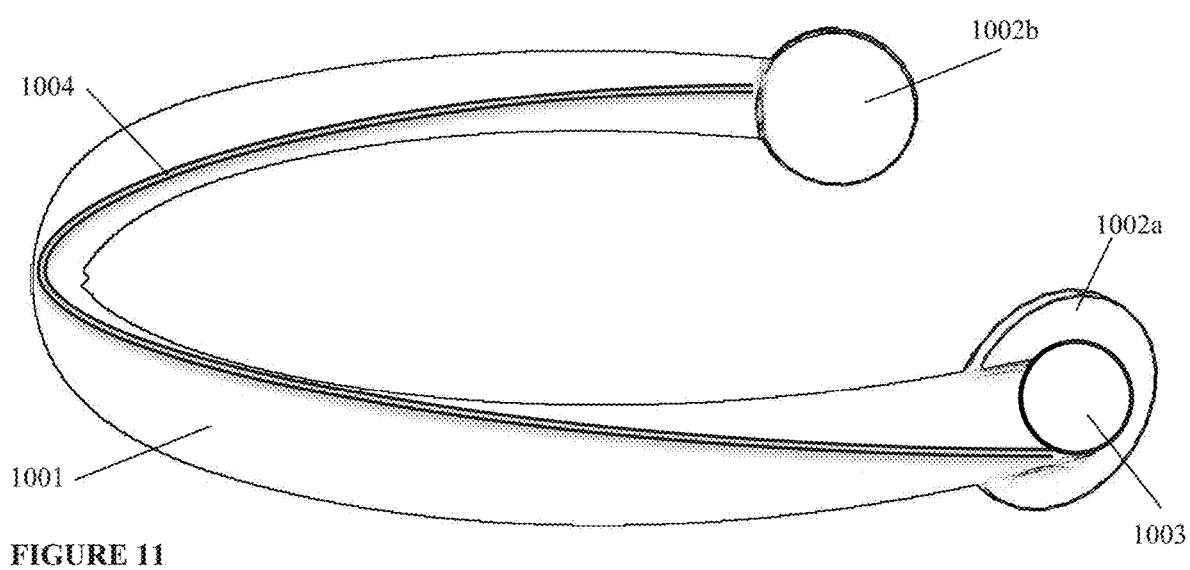
FIG. 11 shows a perspective view of the Modified Hairband for Dual Sensor & Sensor Array.

In FIG. 10, the base structure is a hairband 1001. At the two ends of the hairband, there are two mounts 1002a, 1002b. FIG. 11 shows additional detail. The mounts 1002a, 1002b are connected electrically with wires 1004 to the mount for the CPU/battery 1003.

Figure 12:
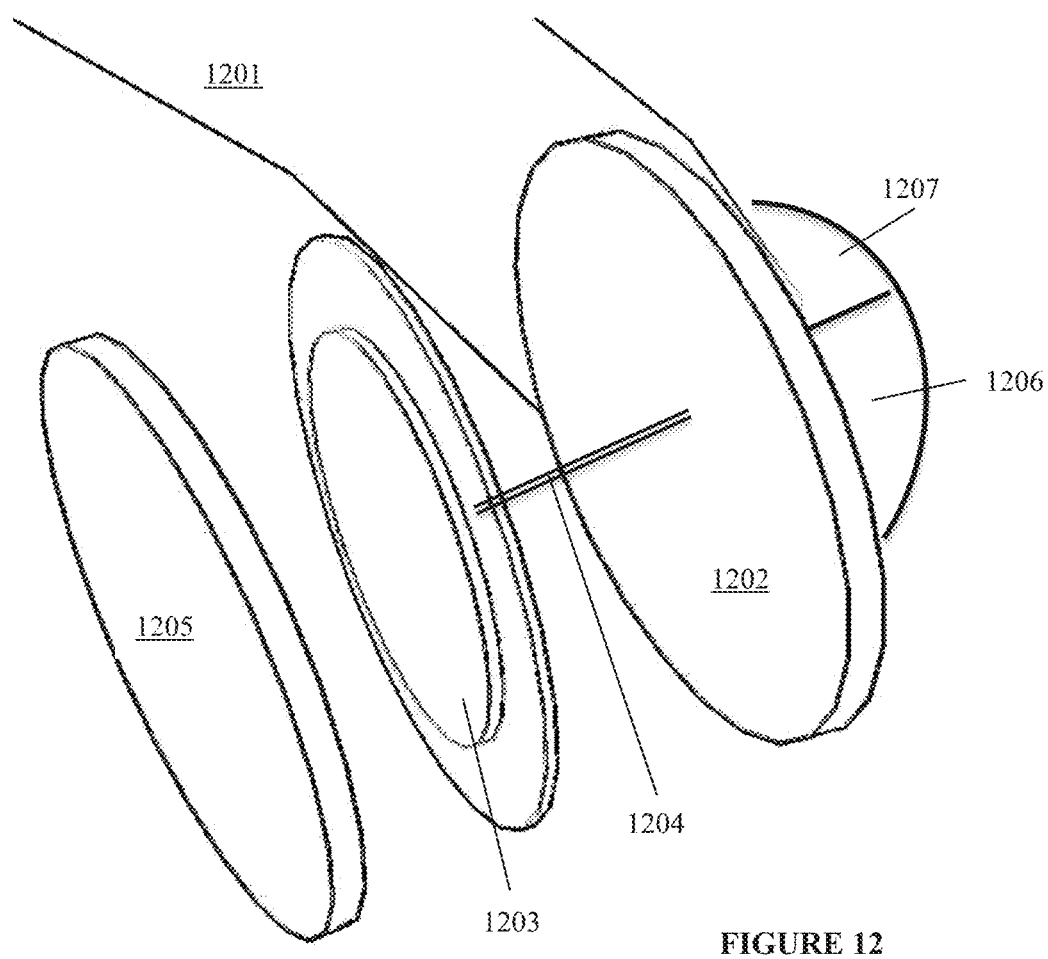
FIG. 12 shows an exploded view of the Modified Hairband for Dual Sensor & Sensor Array.

FIG. 12 is an exploded view of the side of the hairband embodiment. The hairband 1201 holds a mount 1202. The mount 1202 has wires 1204 that electrically connect the two piezo discs 1203 and the CPU 1206. Mechanically, the piezo discs 1203 are inserted into and connected to the mount 1202. A foam cover 1205 covers the piezo disc 1203 and provides comfort to the user. On the other side of the mount 1202 is the mounting for the microprocessor assembly 1206 and the battery 1207.

Figure 13:
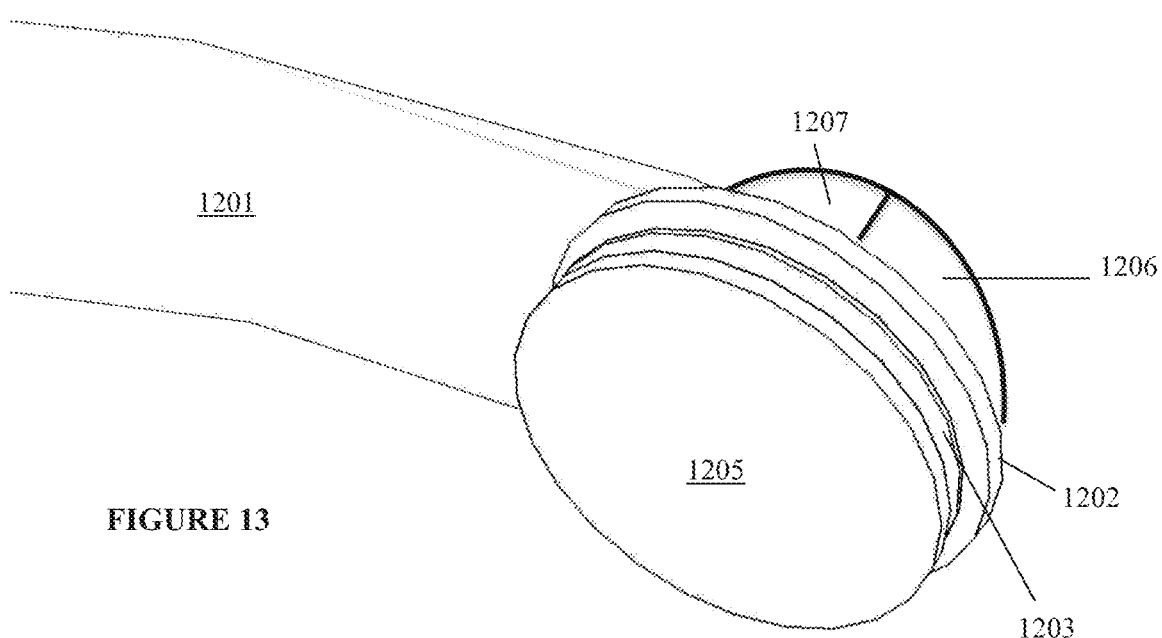
FIG. 13 shows a compact view of the Modified. Hairband for Dual Sensor & Sensor Array.

FIG. 13 shows an assembled view of the hairband embodiment.

Figure 14:
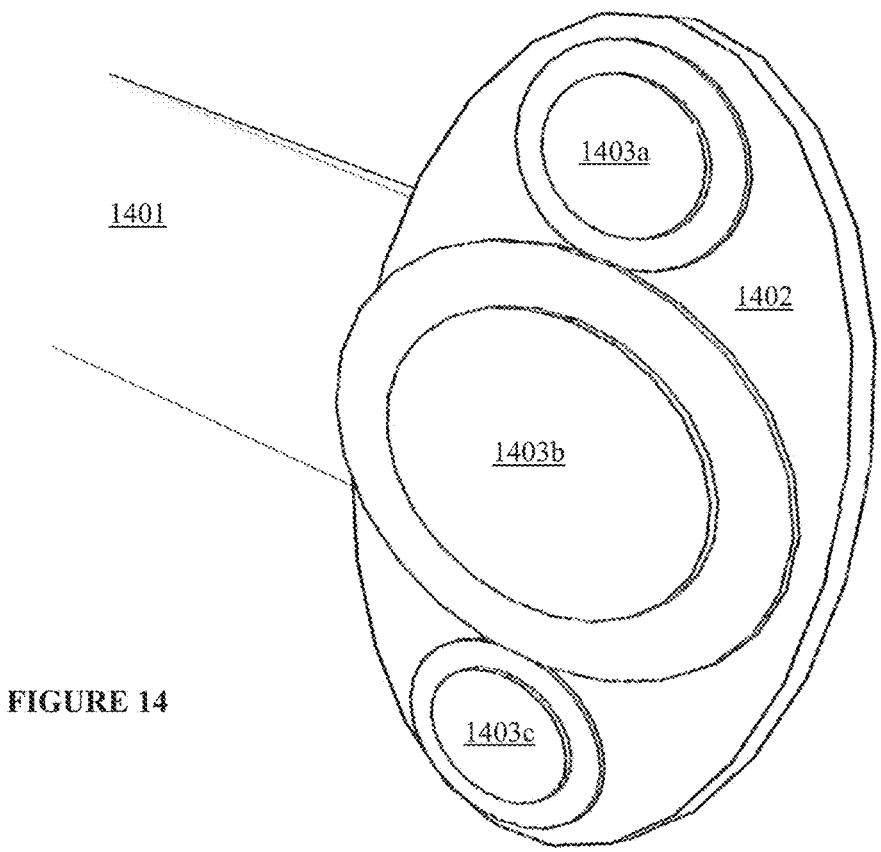
FIG. 14 shows a cross section view of the Sensor Configuration for a Modified Hairband for Dual Sensor.
Figure 15:
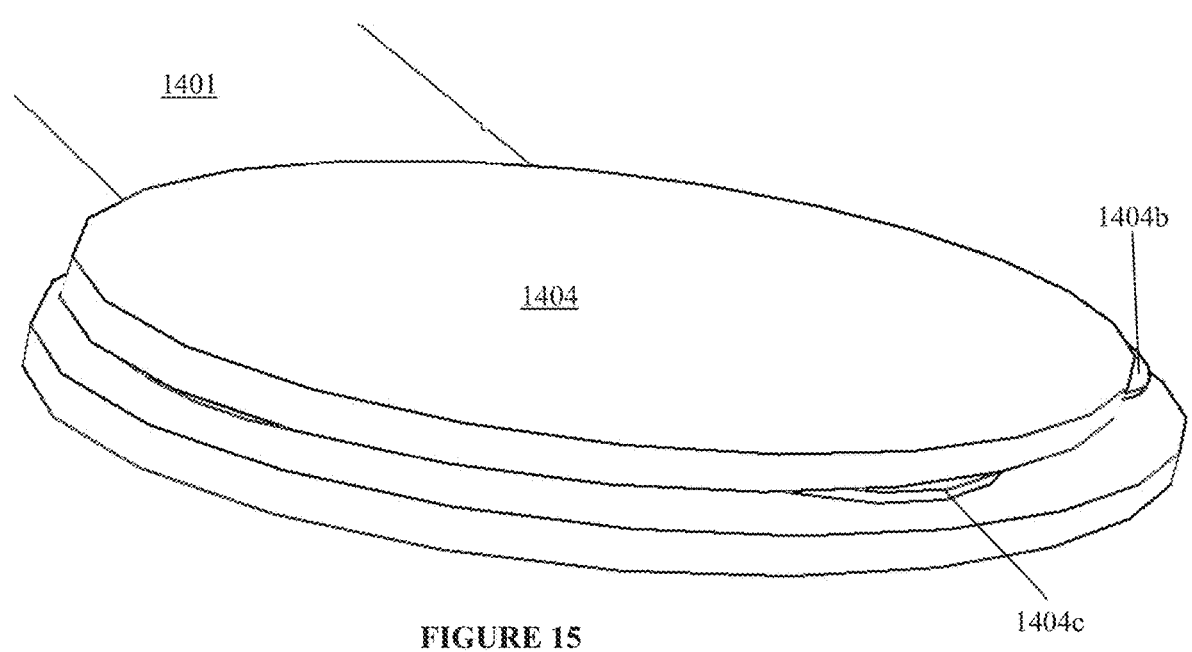
FIG. 15 shows a perspective view of the Sensor Configuration for a Modified Hairband for Dual Sensor.

In a second embodiment of the hairband design, FIGS. 14 and 15 show multiple sensors on the hairband 1401. The hairband 1401 has a mount 1402 for holding two or more piezo sensors 1403a,1403b,1403c or for holding two or more resistive sensors. The piezo sensors 1403a,1403b, 1403c are covered by a foam disc 1404 to provide the patient comfort as the sensors are pressed against the skin.

Figure 16:
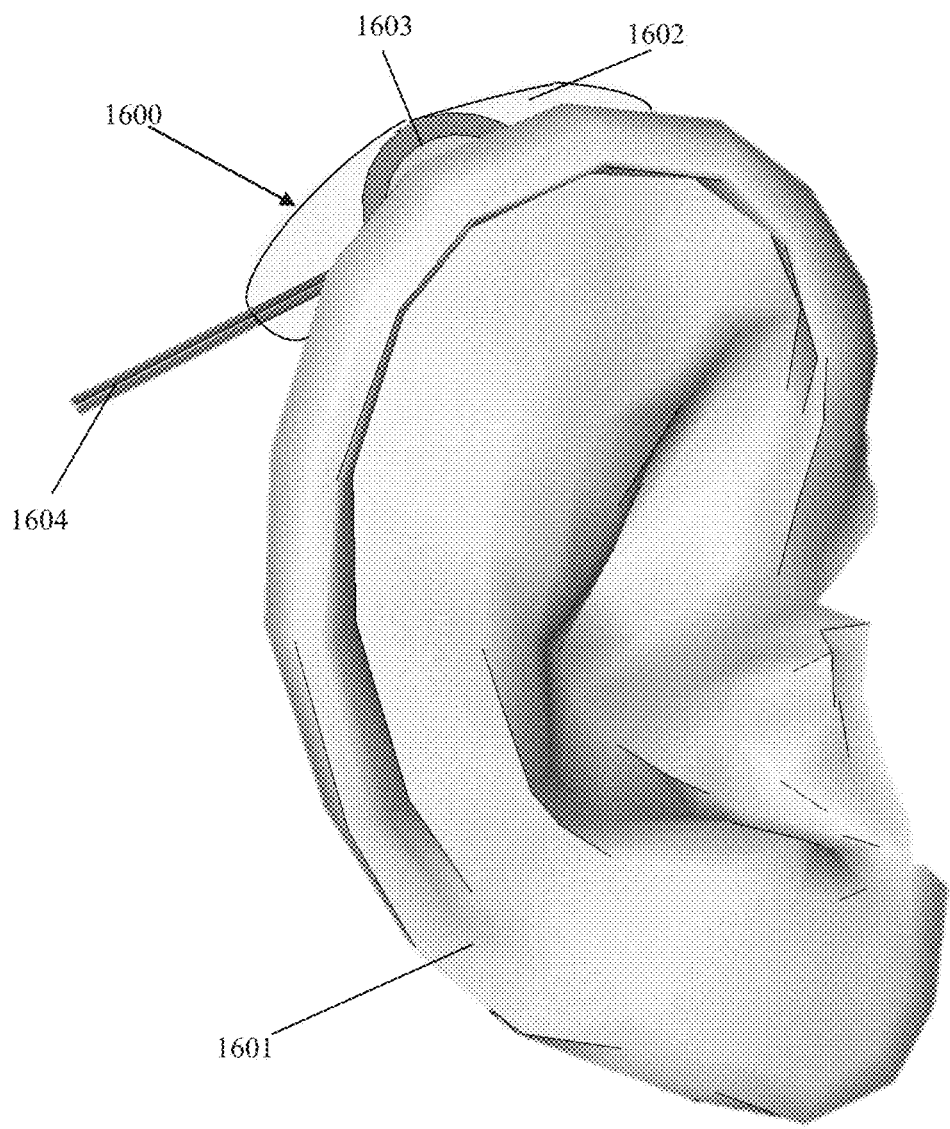
FIG. 16 shows a Method of Sensor Placement: Sticky Piezo Disc Muscle Sensor & Sticky Piezo Film Muscle Sensor in a preferred location of placement.

FIG. 16 shows the placement location of the sticky piezo muscle sensor 1600 or the sticky piezo film muscle sensor in its preferred location of placement. The sensor 1600 is placed behind and at the top of the ear 1601. The sensor 1600, once placed over the desired muscle, works to sense the muscle's contraction by detection pneumatic changes in the shape and tension of the surface skin. Placement of the piezo disc muscle sensor 1600 over the temporalis muscle, just above the ear 1601 is the most desired placement in detecting bruxism. The temporalis muscle just above the ear only contracts when the back teeth are clenched or grinding. Therefore the placement of sensor on the temporalis muscle just above the ear negates any interference the sensor would receive due to normal facial movements like talking or facial expression such as raising one's eyebrows.

The sticky piezo sensor 1600 consists of a plastic base 1602 that adheres to the patient's skin, a piezoelectric sensor 1603 attached to the base 1602, and two wires 1604 to provide the signals from the piezo sensor 1603 to a computer or to a microprocessor for signal conditioning and processing of the signal.

Figure 17:
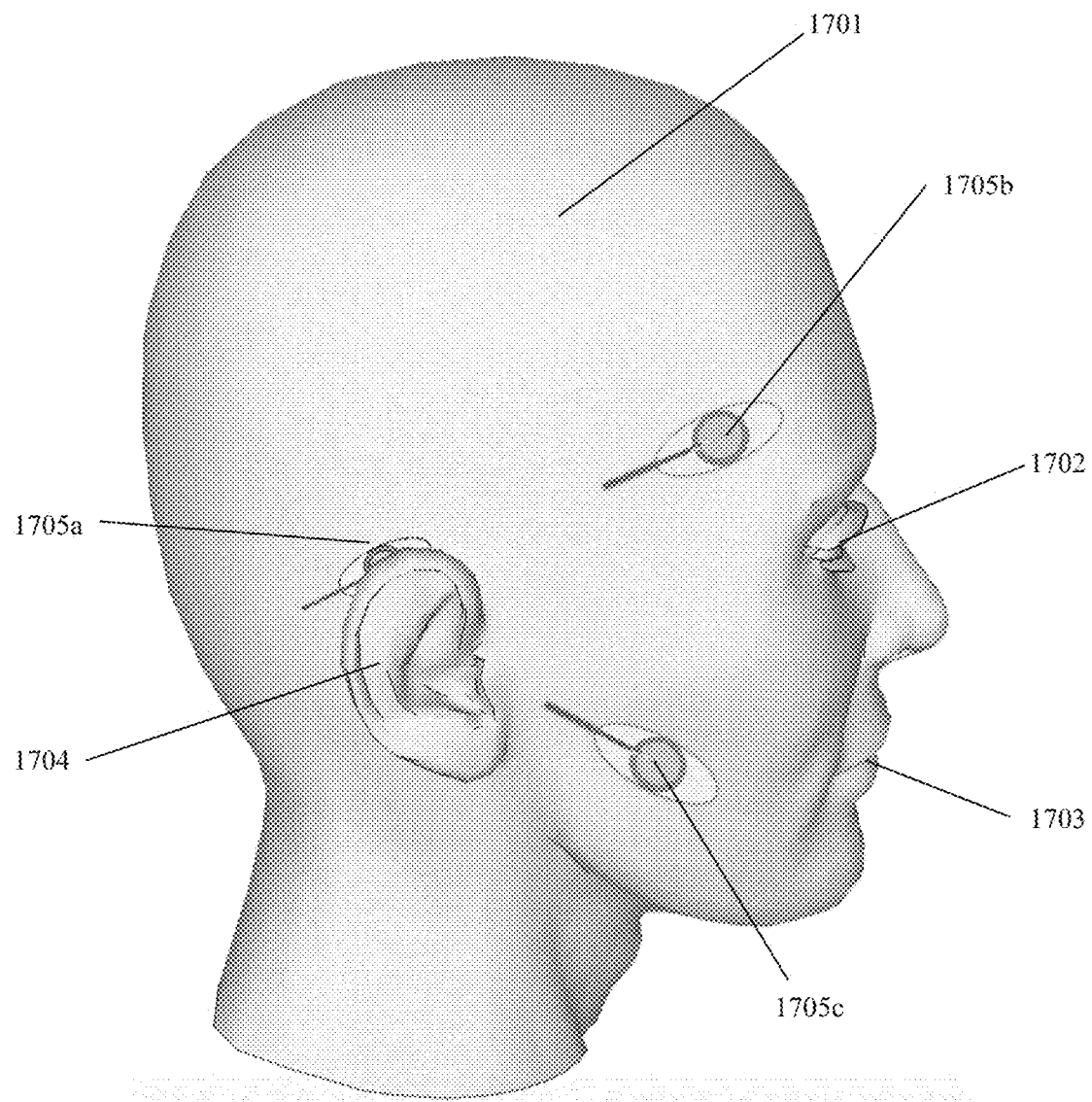
FIG. 17 shows a Method of Sensor Placement for the Sticky Piezo Disc Muscle Sensor & Sticky Piezo Film Muscle Sensor Placement Locations.

FIG. 17 shows additional sensor placements on a human head 1701. As described above for FIG. 16 one sensor 1705a is placed behind the ear 1704 above the temporalis muscle. A second sensor 1705b is placed above and slightly behind the eye 1702 on the front portion of the temporalis muscle. A third sensor 1705c is placed on the jaw muscles behind the mouth 1703 on the masseter muscle.

Figure 18:
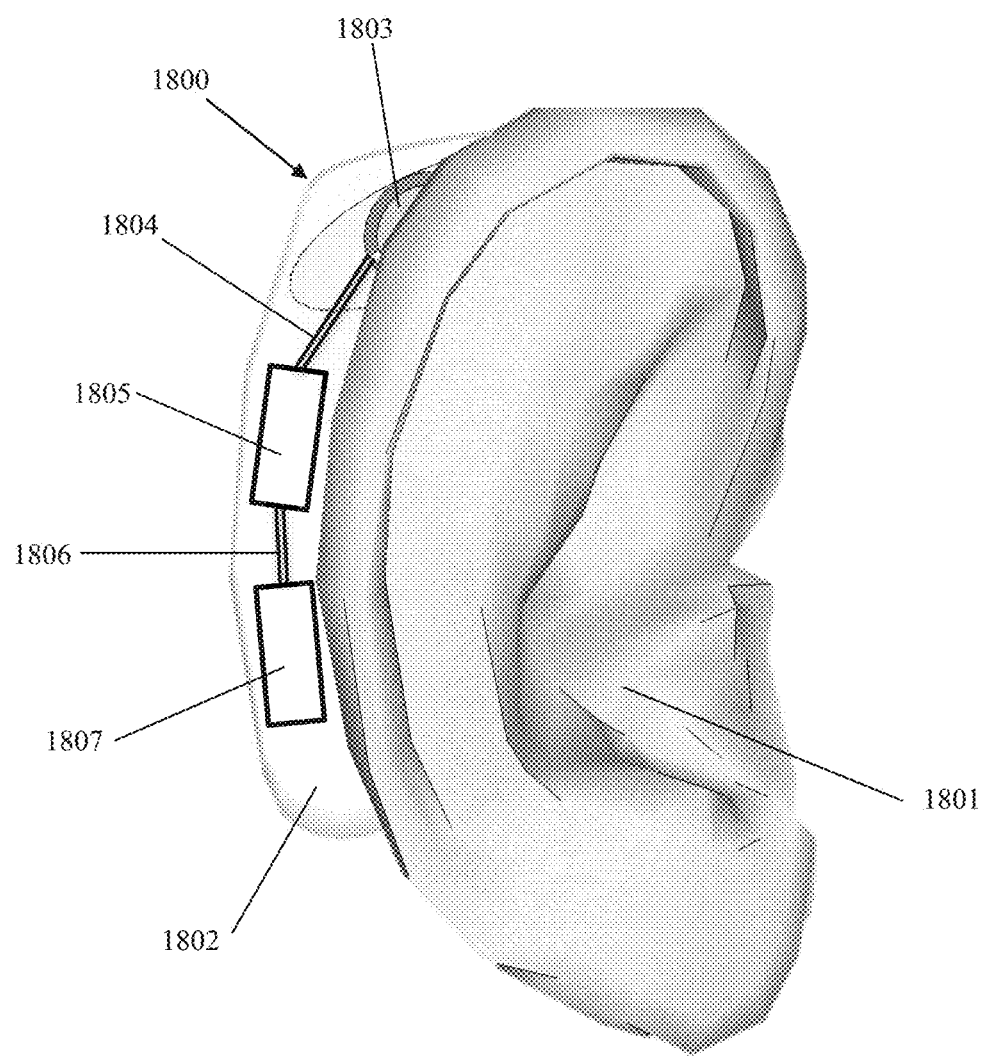
FIG. 18 shows a Method of Sensor Placement for the Piezo Disc Muscle Sensor Encased in Silicone Gel Adhesive w/Micro Controller & Battery-Ear placement.

FIG. 18 is a view of the piezo disc muscle sensor encased in silicone gel 1800 as placed behind the ear 1801, detecting movements of the temporalis muscle. The sensor 1800 encloses a piezo sensor 1803 in a silicone gel sack 1802. The piezo sensor 1803 is connected to a microprocessor assembly 1805 with wires 1804 that deliver the signal from the piezo sensor 1803 to the microprocessor assembly 1805. The microprocessor assembly 1805 is also connected via wires 1806 to a battery 1807, the wires 1806 delivering power to the microprocessor assembly 1805. The microprocessor assembly 1805 is described in further detail in FIG. 23.

Figure 19:
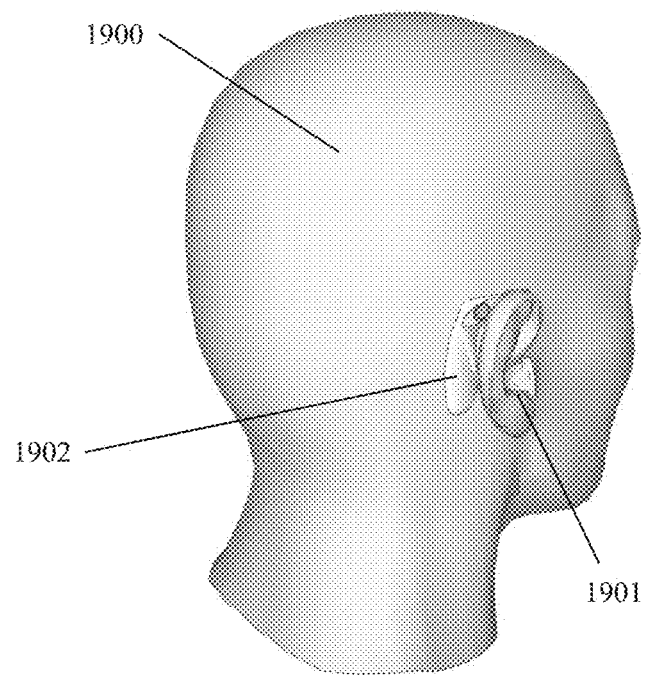
FIG. 19 shows a Method of Sensor Placement for the Piezo Disc Muscle Sensor Encased in Silicone Gel Adhesive-Ear placement, perspective view.
Figure 20:
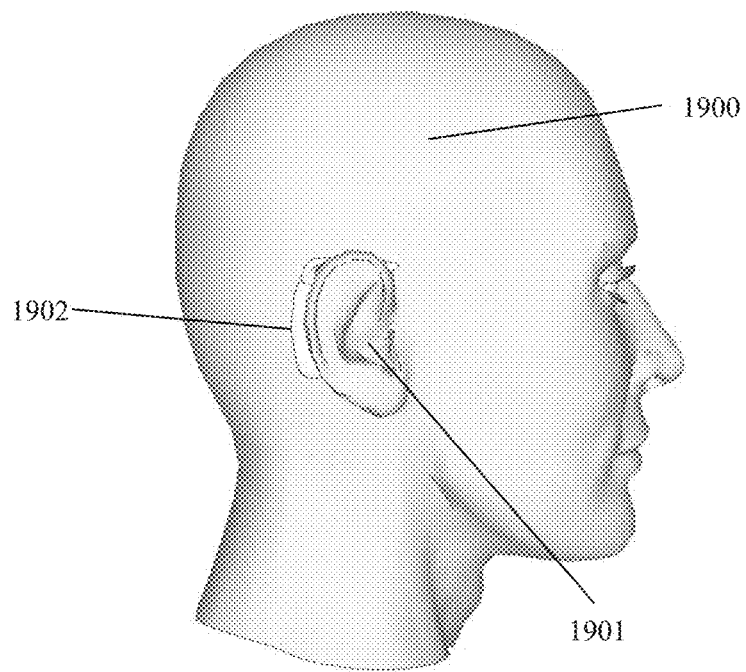
FIG. 20 shows a Method of Sensor Placement for the Piezo Disc Muscle Sensor Encased in Silicone Gel Adhesive w/Micro Controller & Battery-Ear placement, side view.

FIG. 19 is a perspective view of the placement of the piezo disc muscle sensor encased in silicone gel 1902 as placed behind the ear 1901 on the head 1900. The figure shows the sensor 1902 located in such a way to detect movements of the temporalis muscle. Similarly, FIG. 20 shows a side view of the placement of the piezo disc muscle sensor encased in silicone gel 1902 as placed behind the ear 1901 on the head 1900.

Figure 21:
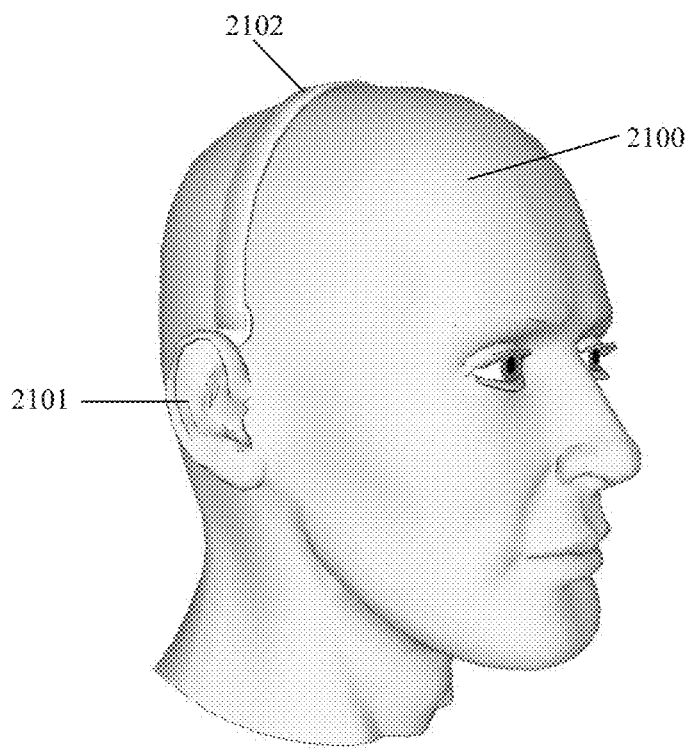
FIG. 21 shows a Method of Placement of the Piezo Disc/Force Sensitive Resistor Hairband Dual Single Sensor & Dual Sensor Array from a front perspective view.

FIGS. 21 and 22 show two different (front and back) perspective views of the hairband embodiments 2102 as placed on a human head 2000. The sensors at the end of the hairband 2102 are positioned behind the ear 2001, sensing movement of the temporalis muscle.

In the present invention, as seen in FIG. 23, this piezo disc muscle sensor assembly 2303 can be directly connected to a micro-electronics controller 2302 board where the signal can be analyzed and interpreted to detect bruxism events. Furthermore, once events of bruxism are detected the controller board can initiate a biofeedback response to the wearer. The biofeedback response can be initiated in various ways.

Sound: a wired piezoelectric buzzer 2308 can be used to alert the wearer that they are grinding or clenching. Alternative a detachable earbud speaker 2309 can be used to signal the wearer discretely if he/she not like to disturb their partner.

Vibration: a small vibration motor 2310 can be wired to the microcontroller unit so that each time the user clenches or grinds their teeth the unit vibrates to alert them.

Mild Electric Impulse: electrodes 2311 can be wired to the microcontroller and used to emit a mild electric impulse to the user to subtly alert the user to unclench their muscle and stop grinding.

The present invention, a bruxism detection and biofeedback device, will utilize a Bluetooth capable microcontroller 2302 and link to the wearer's smartphone 2307 through and Android and IOS app. The wearer will be able to adjust their therapy, adjust the intensity of the vibration or electrical stimulation as well as the volume of the sound. The device working with the wearer's smartphone 2307 will be able to visually track their progress viewing reports on how many times they grinded or clenched their teeth the previous night. Additionally the wearer will be able to see how well their therapy is progressing over time by comparing nightly events of bruxism over the course of several days or weeks.

Electrically, FIG. 23 shows the interconnection between the special purpose microprocessor system on a chip 2302 (perhaps a Cypress Semiconductor PSoC chip or a Fanstel BC832 system on a chip). The microprocessor 2302 could have memory, communications, signal conditioning, battery management and other functions incorporated with the processing capabilities. A battery 2301 is connected to the microprocessor 2302 to provide power. As described above, the battery 2301 could be replaceable, rechargeable, disposable, or could be a non-battery power supply converting vibrations or radio waves into power. The communications functionality of the microprocessor 2302 could produce Bluetooth 2306, WiFi, or Cellular packets to an antenna 2305, The Bluetooth 2306, WiFi, or Cellular signals provide a communications path to a cell phone 2307 or to another computing device.

In one embodiment, the inputs to the microprocessor 2302 are from the piezo sensor 2303 (either the piezo disc or the piezo film). The piezo sensor 2303 is connected to the microprocessor 2303 with one wire and the other wire is attached to ground. A resistor, perhaps 100 K ohm or 1 M ohm is connected in parallel to the piezo sensor. The signal may also need to be amplified (or limited) with an op amp circuit, depending on the range of the microprocessor 2302 inputs and the range of signal coming from the piezo material.

The force sensing resistor 2304 is connected to the microprocessor 2302 in another embodiment. One lead of the sensing resistor 2304 is connected to power (Vcc) and the other lead is connect to two places. One connection is to a resister (Rm) that also connects to ground on the other end. The other connection is to the microprocessor 2302 input pin. This is a voltage divider circuit across the two resistors. Depending on the signal at the input pin and the range capabilities of the input pin, an op amp circuit may be needed to boost or limit the signal.

To provide the feedback to the patient, the microprocessor 2302 has several output devices that could be connected. In one embodiment, a piezo buzzer 2308 is connected to create a buzzing sound to notify the patient that he is grinding his teeth. In another embodiment, a speaker 2309 is connected to the microprocessor 2303. Another embodiment uses a motor 2310 to create vibrations to notify the patient. In still another embodiment, two electrodes are connected to the microprocessor 2302 and to the patient, providing a small electrical shock when the patient is grinding his teeth. An amplifier circuit may be needed in this embodiment to boost the shock to a level that the patient can feel the shock.

Figure 24:
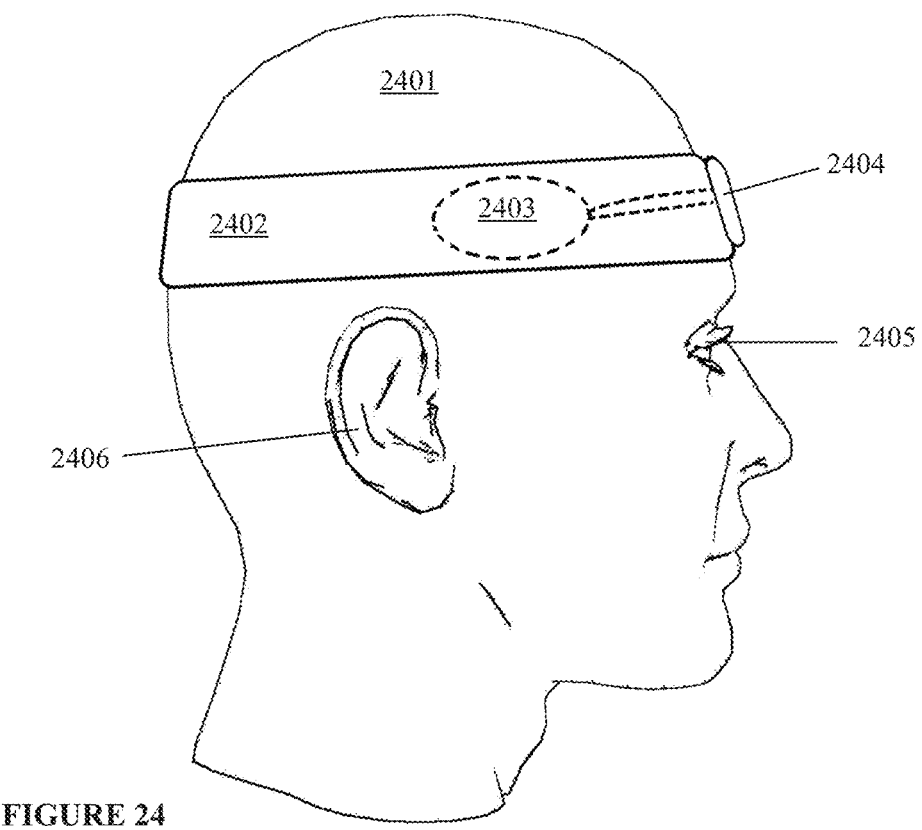
FIG. 24 is a side view of a head with the headband embodiment.
Figure 25:
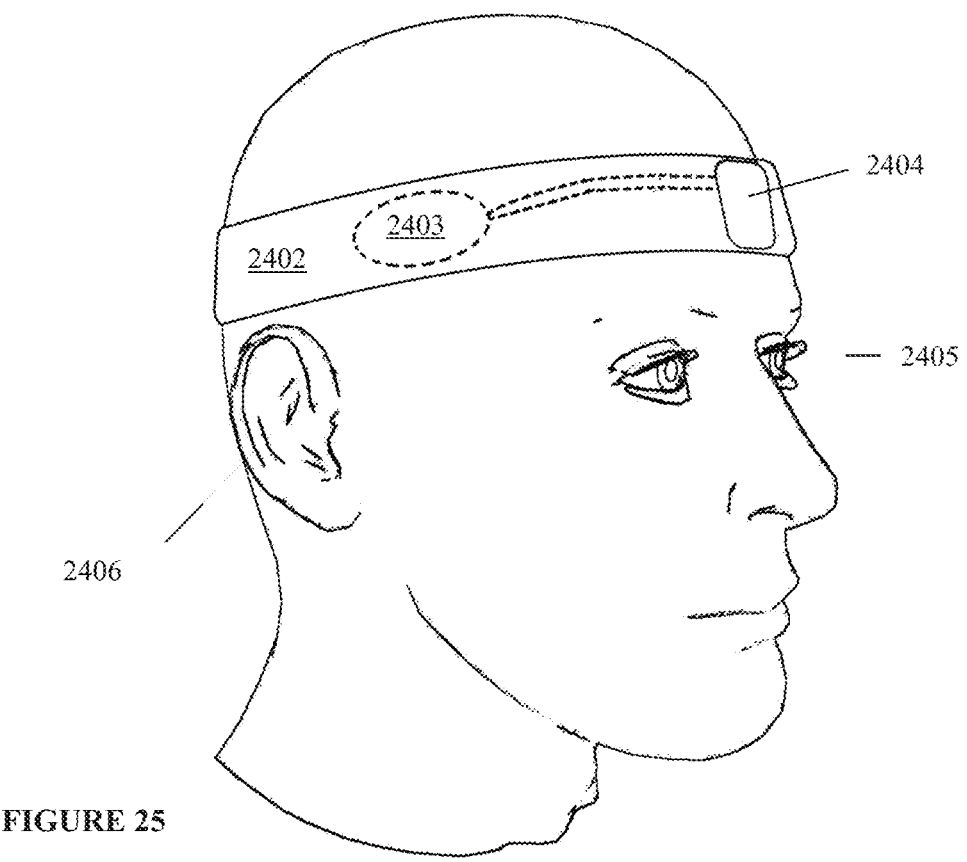
FIG. 25 is a perspective view of the headband embodiment.

In another embodiment, seen in FIGS. 24 and 25, a headband that surrounds the headband 2402 is used to completely surround the head 2401. In this embodiment, the band 2402 would go from low on the back of the head 2401, over or behind the ears 2406 and over the top front of the head 2401. The sensors 2403 could be placed above and in front of the ears 2406 and behind and above the eyes 2405 to detect movements of the temporalis muscle. The microprocessor assembly and battery 2404 could be on the forehead above the eyes 2405. The headband 2402 may be adjustable to allow for a fit to the patients head 2401. In one embodiment, there could be a piezoelectric sensor 2403 mounted on each side of the headband 2402, sensing movement of the temporalis muscle on both sides of the head.

In still another embodiment, the apparatus could be constructed out of a modified sleep mask. The mask would cover the eyes and contain the electronics and biofeedback vibration motor and the sensors would incorporated into the elastic band that holds the sleep mask. Just as in the headband embodiment, the sensors would be placed over the temporalis muscle.

The foregoing devices and operations, including their implementation, will be familiar to, and understood by, those having ordinary skill in the art.

The above description of the embodiments, alternative embodiments, and specific examples, are given by way of illustration and should not be viewed as limiting. Further, many changes and modifications within the scope of the present embodiments may be made without departing from the spirit thereof, and the present invention includes such changes and modifications.

The invention claimed is:

1. A method of detecting bruxism comprising:
arranging a pressure resistive sensor proximate to skin above a temporalis muscle, wherein the pressure resistive sensor comprises:
carbon-impregnated polyolefin material with a first side and a second side, wherein the polyolefin material comprises at least five carbon-impregnated polyolefin surfaces;
a first conductive surface attached to the first side of the polyolefin material;
a second conductive surface attached to the second side of the polyolefin material;
a first wire connected to the first conductive surface; and
a second wire connected to the second conductive surface;

sensing movement of the temporalis muscle with the pressure resistive sensor;
transmitting information related to the movement through the first wire and the second wire to a special purpose microprocessor; and
analyzing the movement information within the microprocessor to determine if the bruxism is occurring.

2. The method of claim 1 wherein the polyolefin material comprises multiple carbon-impregnated polyolefin surfaces stacked on top of each other.

3. The method of claim 2 wherein the multiple carbon-impregnated polyolefin surfaces are adhered with an adhesive.

4. The method of claim 1 wherein the pressure resistive sensor is arranged using a headband mechanically connected to the pressure resistive sensor.

5. The method of claim 1 further comprising providing biofeedback when the bruxism is determined.

6. The method of claim 5 wherein the biofeedback is provided by creating a sound through a speaker connected to the special purpose microprocessor.

7. A muscle contraction sensor comprising:
carbon-impregnated polyolefin material with a first side and a second side, wherein the polyolefin material comprises at least five carbon-impregnated polyolefin surfaces;
a first conductive surface attached to the first side of the polyolefin material;
a second conductive surface attached to the second side of the polyolefin material;
a first wire connected to the first conductive surface; and
a second wire connected to the second conductive surface;
wherein the second side of the polyolefin material is placed proximate to skin above a muscle.

8. The muscle contraction sensor of claim 7 wherein the polyolefin material comprises multiple carbon-impregnated polyolefin surfaces stacked on top of each other.

9. The muscle contraction sensor of claim 8 wherein the multiple carbon-impregnated polyolefin surfaces are adhered with an adhesive.

10. The muscle contraction sensor of claim 7 wherein the muscle is a temporalis muscle.

11. The muscle contraction sensor of claim 7 further comprising a headband connected to the first side of the polyolefin material.

12. The muscle contraction sensor of claim 7 wherein the second side of the polyolefin material further comprises an adhesive compatible for attachment to human skin.

13. The muscle contraction sensor of claim 7 further comprising a special purpose microprocessor connected to the first wire and the second wire.

14. The muscle contraction sensor of claim 13 wherein the special purpose microprocessor analyzes signals on the first wire and the second wire to determine if bruxism symptoms are seen in the muscle.

15. The muscle contraction sensor of claim 14 further comprising a biofeedback device connected to the special purpose microprocessor.

16. A pressure sensor comprising:
polyolefin material wherein the polyolefin material comprises multiple carbon-impregnated polyolefin surfaces adhered together, wherein the polyolefin material comprises at least five carbon-impregnated polyolefin surfaces;
a first conductive surface attached to one side of the polyolefin material;

a second conductive surface attached to a second side of the polyolefin material;

a first wire connected to the first conductive surface; and a second wire connected to the second conductive surface.

17. The pressure sensor of claim 16 wherein the multiple carbon-impregnated polyolefin surfaces are adhered with an adhesive.

18. The muscle contraction sensor of claim 7 wherein the first conductive surface and the second conductive surface are attached to the same carbon-impregnated polyolefin surface.

19. The pressure sensor of claim 16 wherein the first conductive surface and the second conductive surface are attached to the same carbon-impregnated polyolefin surface.

* * * * *